(12) United States Patent
de los Reyes

(10) Patent No.: US 8,506,802 B1
(45) Date of Patent: Aug. 13, 2013

(54) STACKABLE PLANAR ADSORPTIVE DEVICES

(75) Inventor: Gastón de los Reyes, Somerville, MA (US)

(73) Assignee: Gaston de los Reyes, Somerville, MA (US)

(*) Notice: Subject to any disclaimer, the term of this patent is extended or adjusted under 35 U.S.C. 154(b) by 273 days.

(21) Appl. No.: 13/013,807

(22) Filed: Jan. 25, 2011

Related U.S. Application Data

(60) Provisional application No. 61/297,896, filed on Jan. 25, 2010.

(51) Int. Cl.
*B01D 15/08* (2006.01)

(52) U.S. Cl.
USPC ............. 210/198.2; 210/198.3; 210/656; 210/658

(58) Field of Classification Search
USPC .......... 210/635, 656, 658, 659, 198.2, 198.3, 210/264, 291
See application file for complete search history.

(56) References Cited

U.S. PATENT DOCUMENTS

| | | | |
|---|---|---|---|
| 3,189,541 A * | 6/1965 | Brenner et al. ............ 210/658 |
| 3,503,712 A * | 3/1970 | Sussman ................. 422/601 |
| 3,782,078 A * | 1/1974 | Jerpe ..................... 96/104 |
| 3,949,806 A * | 4/1976 | Dunges ................... 165/61 |
| 4,248,904 A * | 2/1981 | Fenimore ............... 427/2.11 |
| 4,346,001 A * | 8/1982 | Tyihak et al. .......... 210/198.3 |
| 4,469,601 A * | 9/1984 | Beaver et al. ............ 210/658 |
| 4,551,251 A * | 11/1985 | Kolobow et al. .......... 210/635 |
| 4,591,524 A * | 5/1986 | Tyihak et al. ............ 428/167 |
| 4,671,870 A * | 6/1987 | Tompa et al. ............ 210/149 |
| 4,671,871 A * | 6/1987 | Szekely et al. ........ 210/198.3 |
| 4,879,316 A * | 11/1989 | Alexandratos et al. ...... 521/27 |
| 5,139,680 A * | 8/1992 | Tarnopolsky ............ 210/656 |
| 5,248,428 A * | 9/1993 | Hagen et al. ............ 210/656 |
| 5,766,460 A * | 6/1998 | Bergstrom et al. ...... 210/198.2 |
| 5,772,875 A * | 6/1998 | Pettersson et al. ...... 210/198.2 |
| 6,068,684 A * | 5/2000 | Overton ................. 96/104 |
| 6,652,966 B1 * | 11/2003 | Hin et al. ............... 428/370 |
| 6,936,167 B2 * | 8/2005 | Hobbs et al. .......... 210/198.2 |
| 7,291,263 B2 * | 11/2007 | Ward et al. ............ 210/198.2 |
| 2001/0038831 A1 * | 11/2001 | Park et al. ............. 424/78.31 |
| 2003/0150806 A1 * | 8/2003 | Hobbs et al. ............ 210/635 |
| 2004/0089607 A1 * | 5/2004 | Hobbs et al. ............ 210/656 |
| 2004/0104156 A1 * | 6/2004 | Kolesinski et al. ...... 210/198.2 |
| 2004/0234571 A1 * | 11/2004 | Jang ..................... 424/423 |
| 2005/0006293 A1 * | 1/2005 | Koehler et al. ......... 210/198.2 |
| 2005/0126985 A1 * | 6/2005 | Campbell et al. ......... 210/436 |
| 2008/0135484 A1 * | 6/2008 | Hammer ................. 210/656 |
| 2008/0283458 A1 * | 11/2008 | Ishii et al. ............. 210/198.2 |
| 2012/0118807 A1 * | 5/2012 | Natarajan .............. 210/198.2 |

* cited by examiner

*Primary Examiner* — Ernest G Therkorn
(74) *Attorney, Agent, or Firm* — Chapin IP Law, LLC

(57) ABSTRACT

Stackable planar adsorption devices include a plurality of layers of adsorptive media provided in a web format. The layers are stacked in contiguous fashion, sealed and include fluid passageways to provide a range of scalable chromatography devices suitable for large scale manufacturing applications.

13 Claims, 16 Drawing Sheets

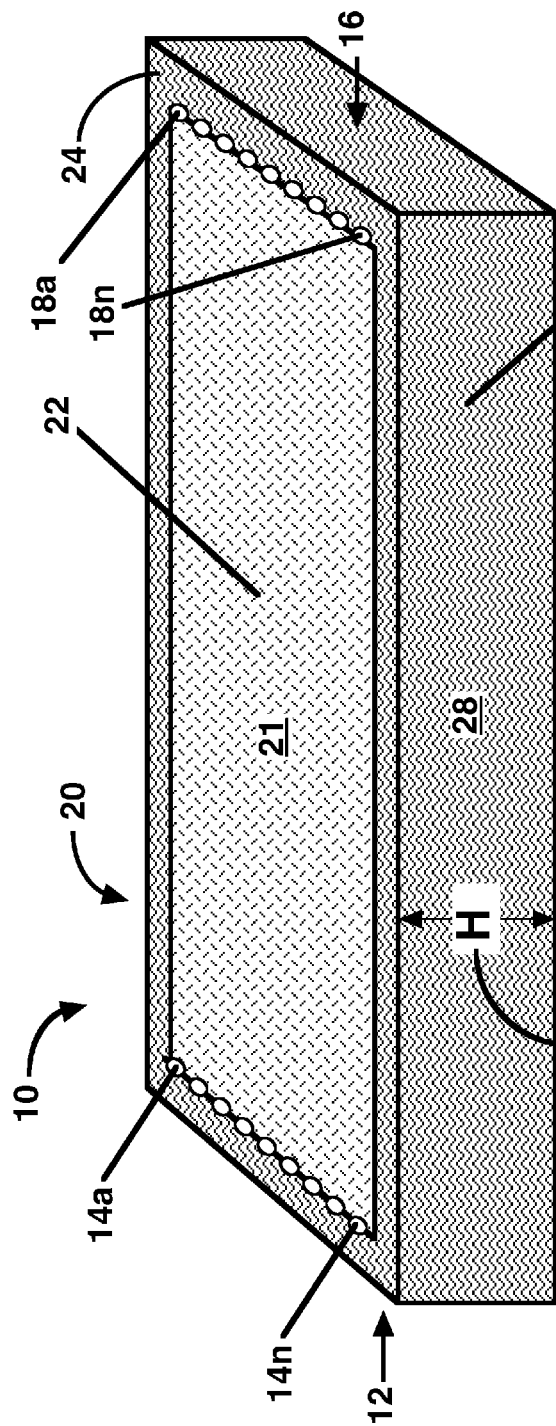
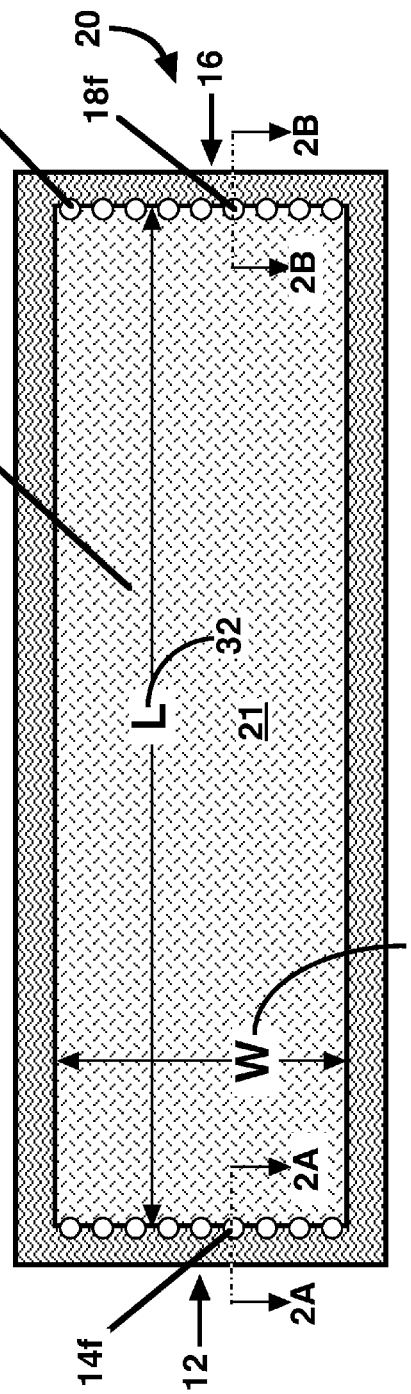
Fig. 1A
Fig. 1B

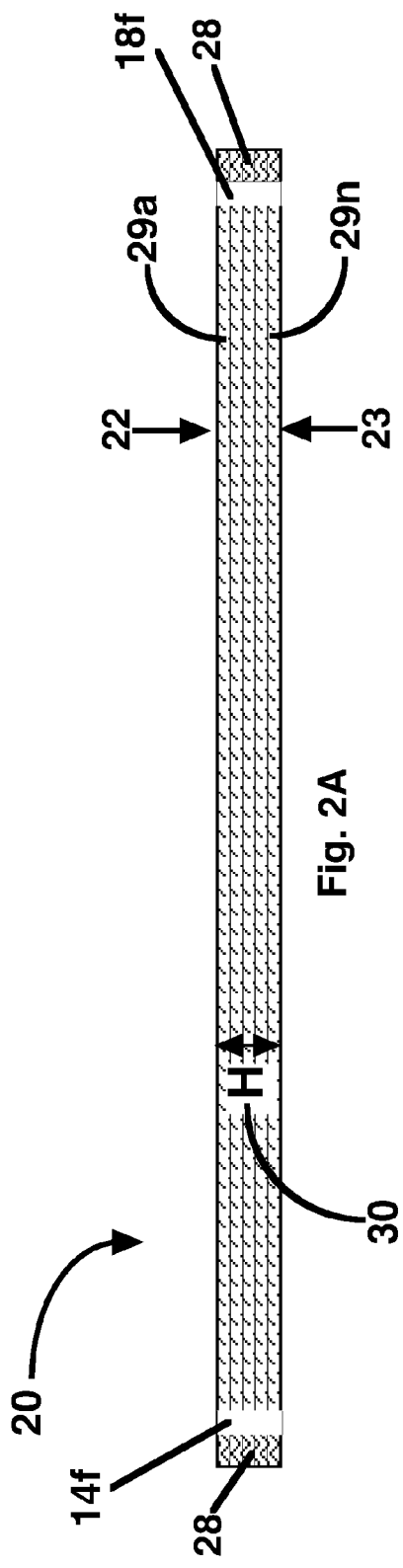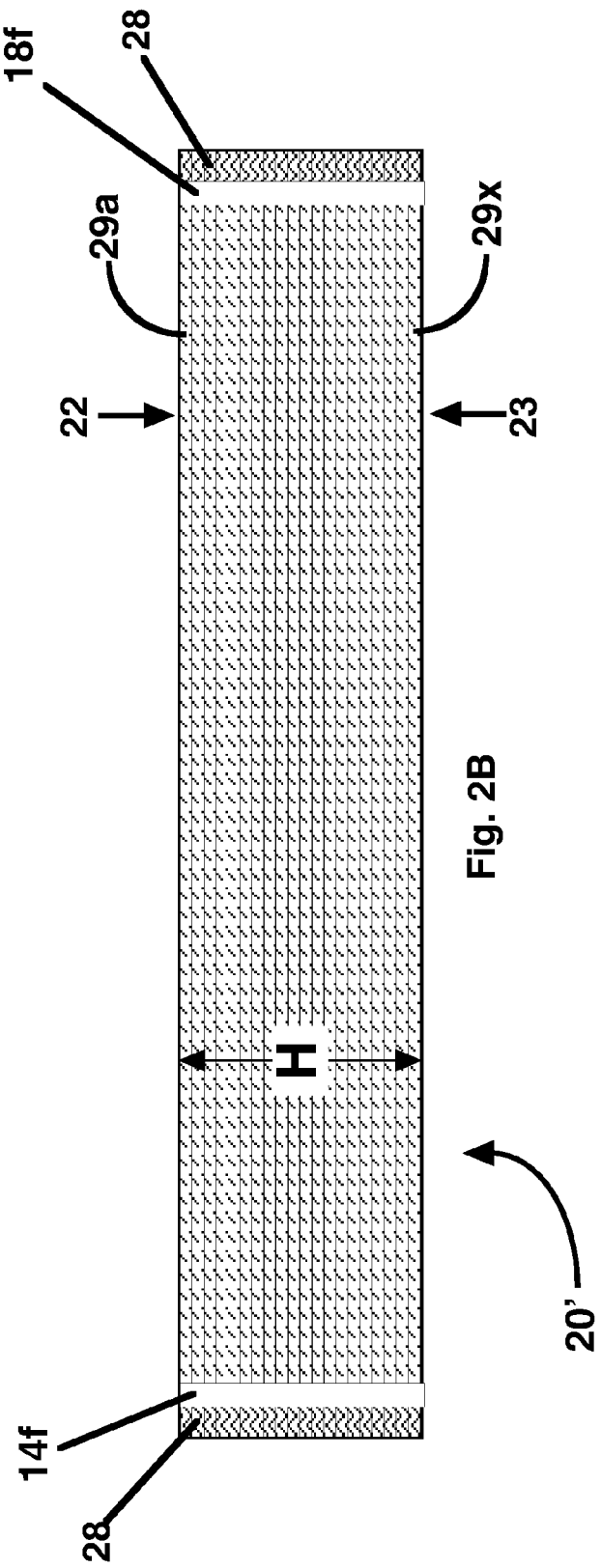

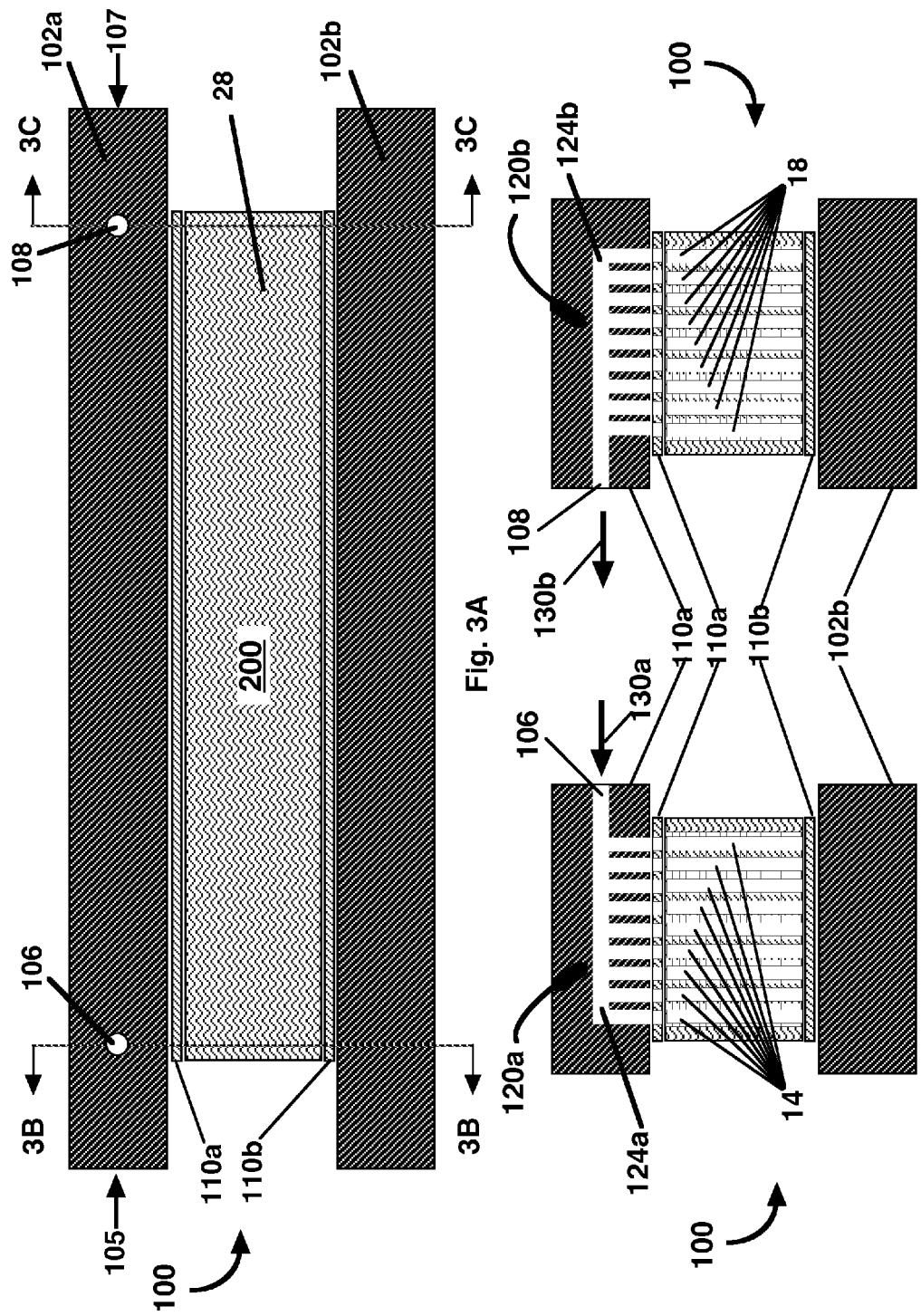

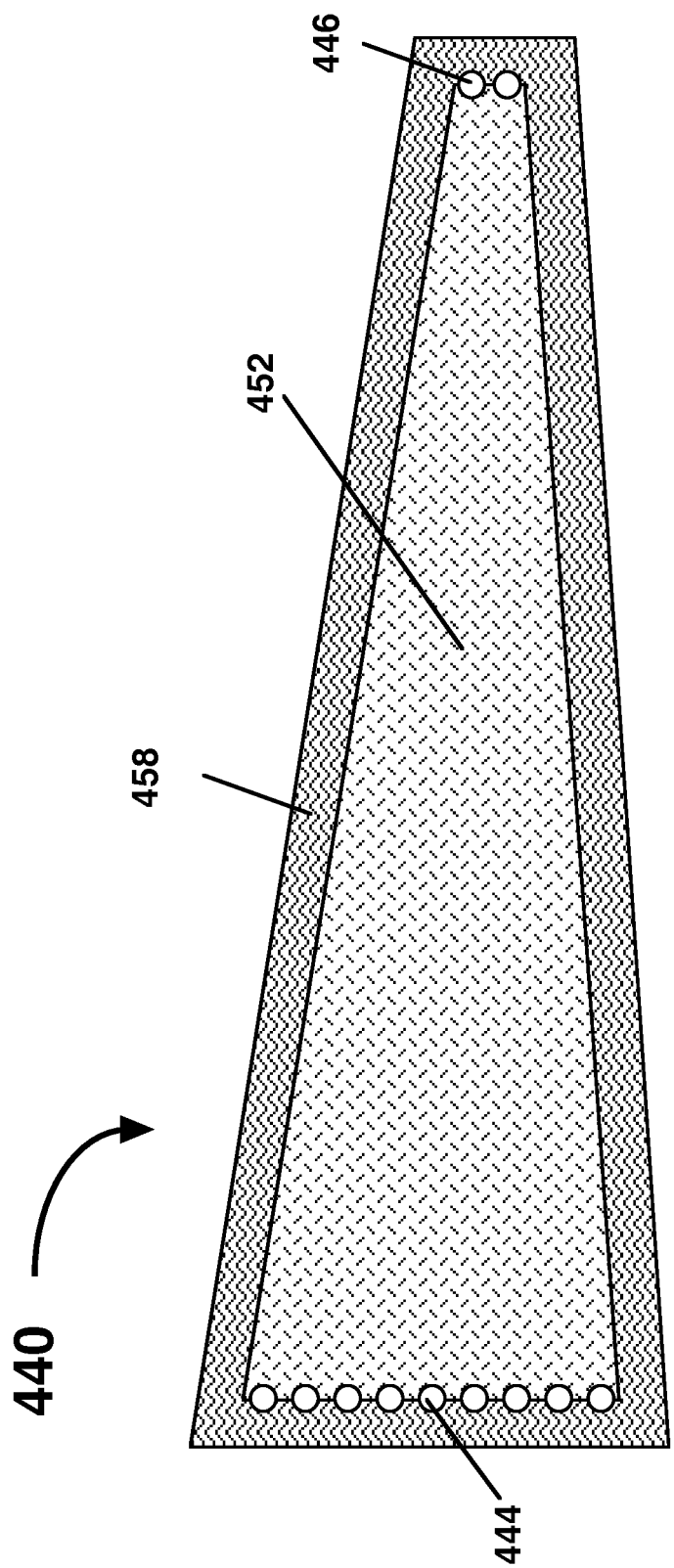

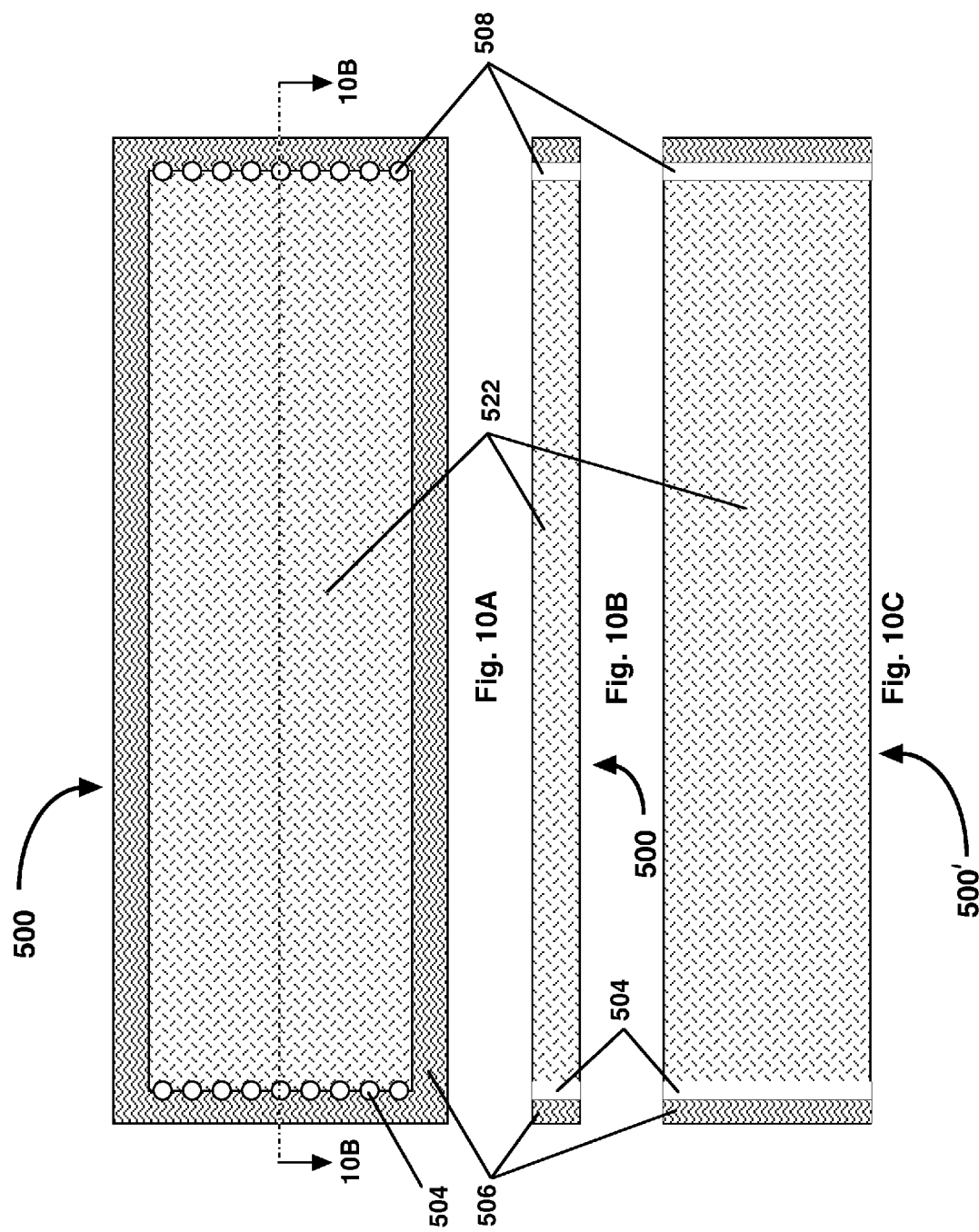

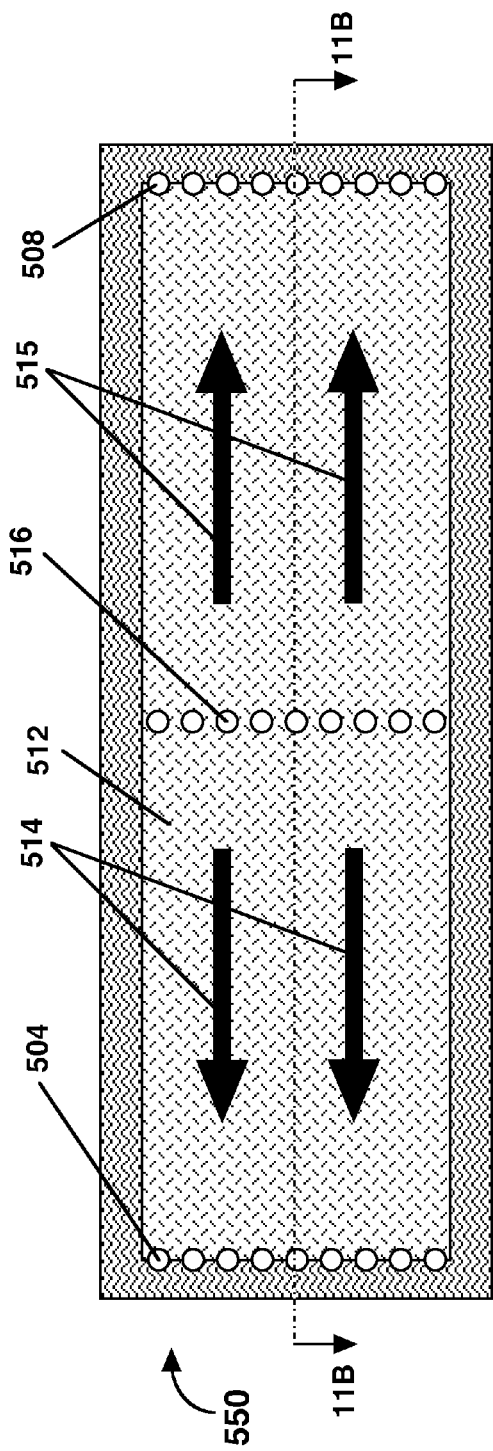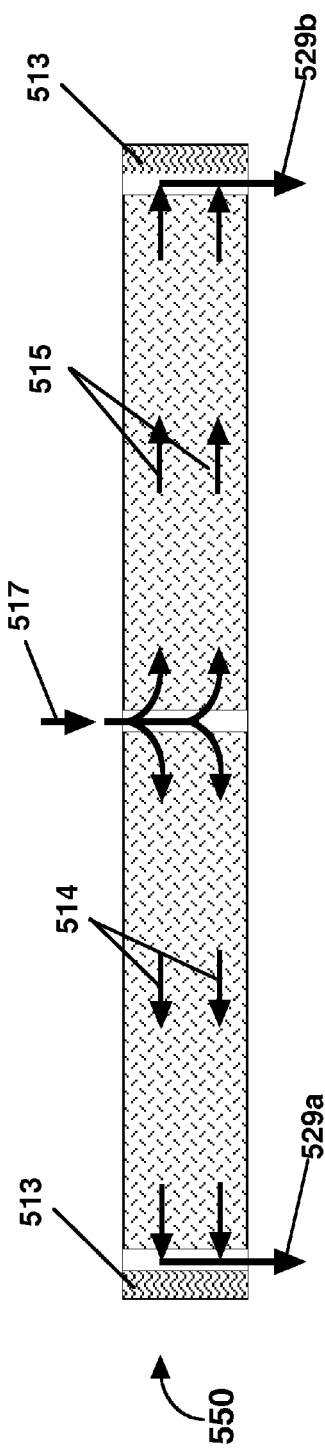

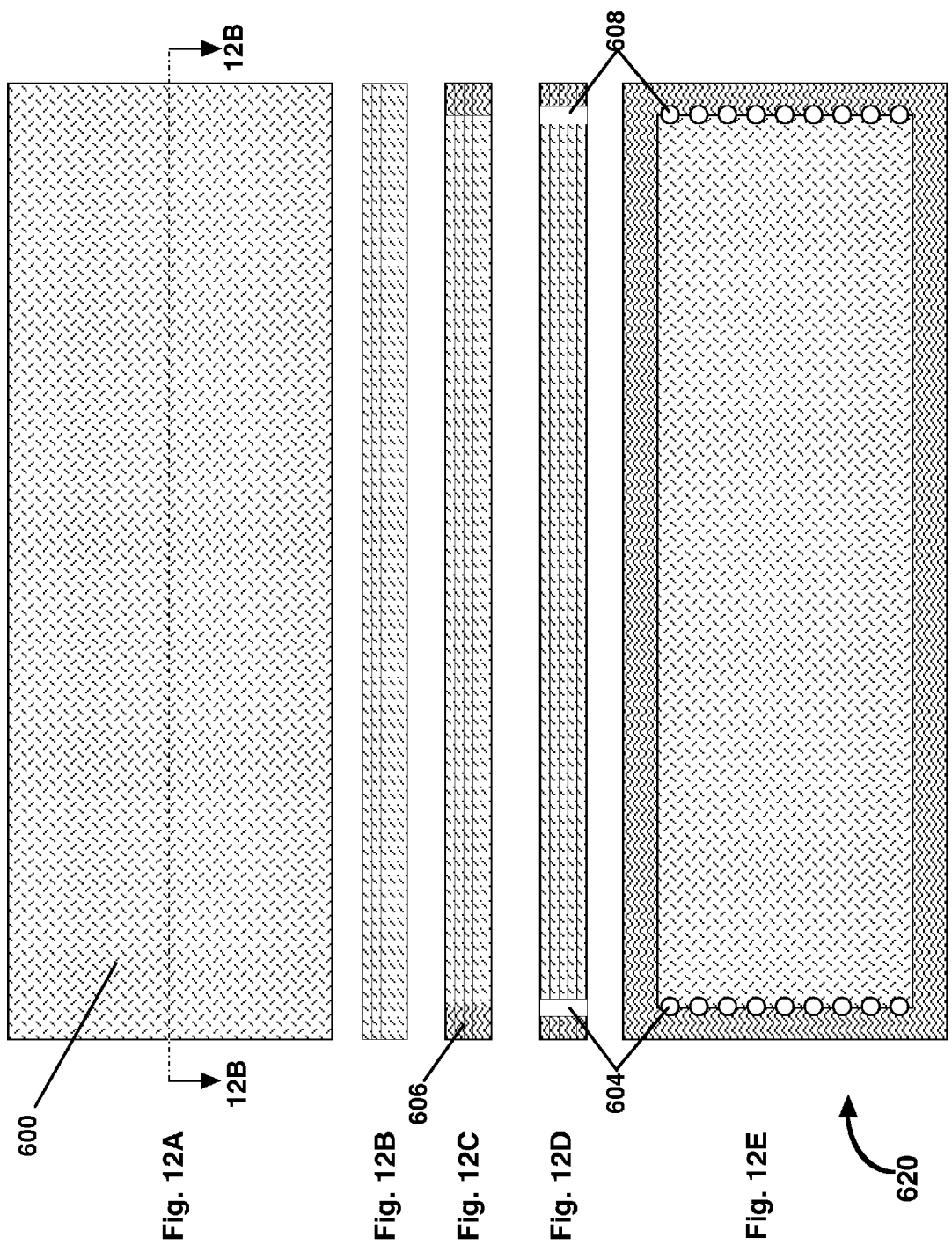

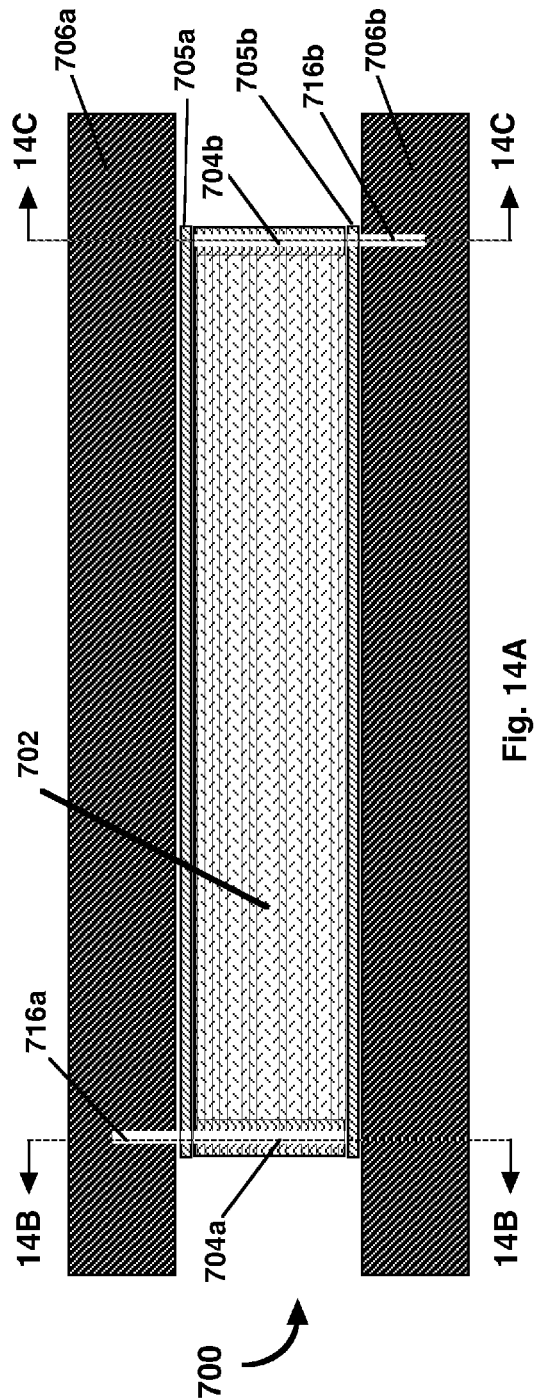
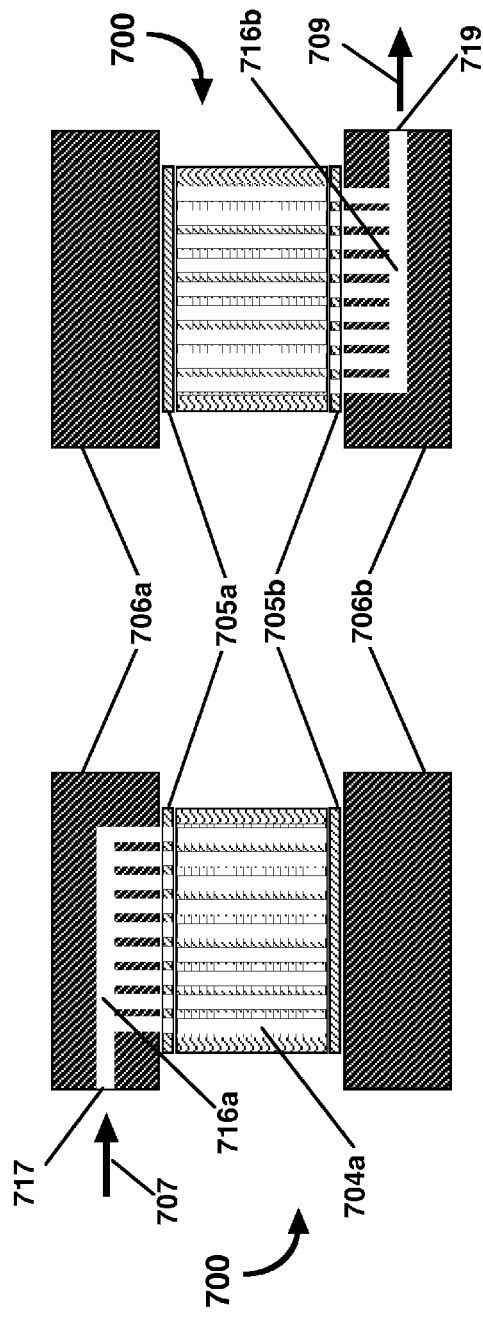
Fig. 14A
Fig. 14B
Fig. 14C

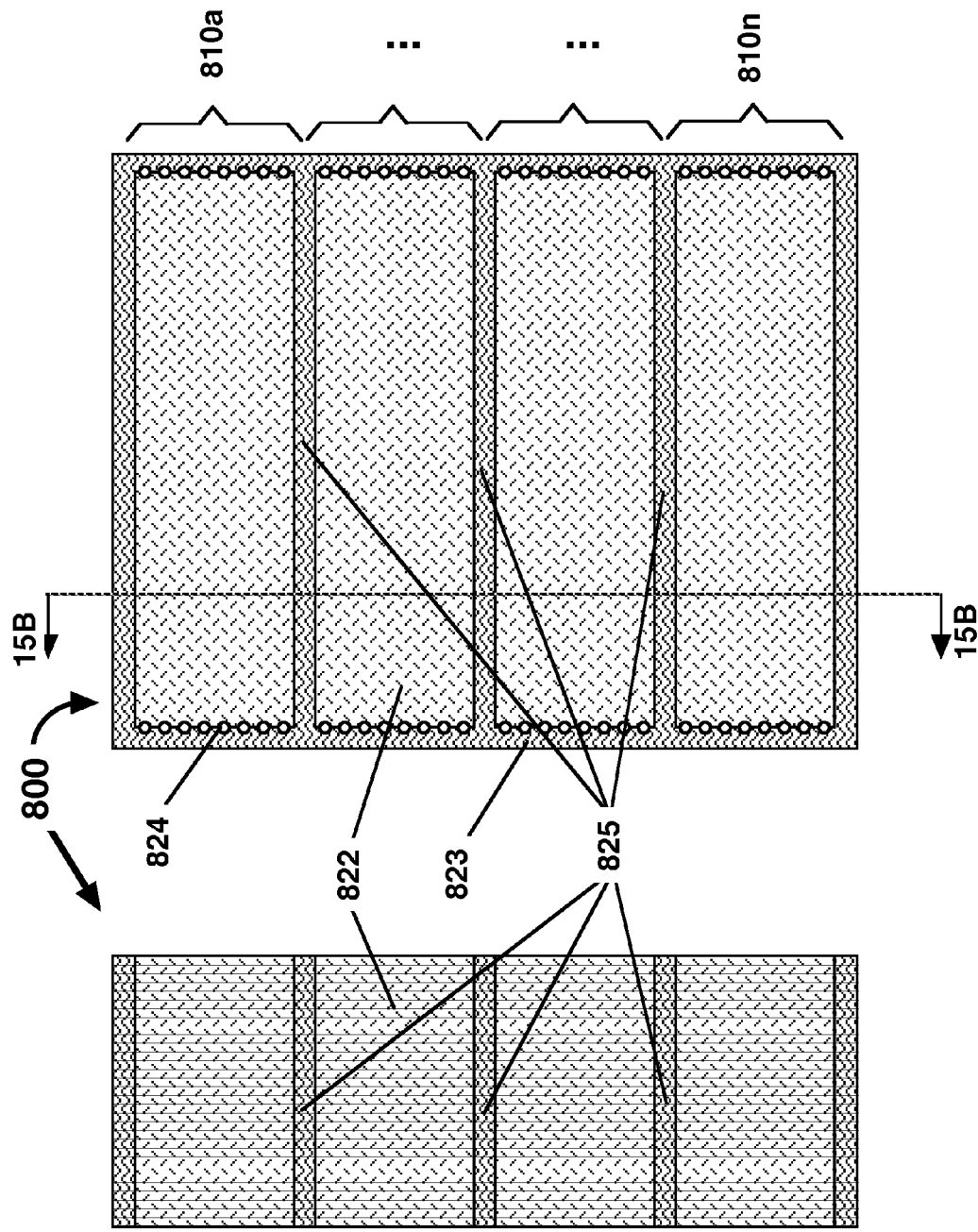

STACKABLE PLANAR ADSORPTIVE DEVICES

CROSS-REFERENCE TO RELATED APPLICATIONS

This application claims the benefit of U.S. Provisional Application No. 61/297,896, filed Jan. 25, 2010, which is incorporated by reference in its entirety.

TECHNICAL FIELD

The field of this invention is related to absorptive devices and processes, of which chromatography is an example. More specifically, this invention relates to planar adsorptive processes and devices having planarly cohesive adsorptive media.

BACKGROUND OF THE INVENTION

Adsorptive processes and devices are widely used in the analysis and purification of chemicals, including synthetic and naturally-derived pharmaceuticals, blood products and recombinant proteins.

Chromatography is a general separation technique that relies on the relative affinity or distribution of the molecules of interest between a stationary phase and a mobile phase for molecular separation. The stationary phase typically comprises a porous media imbibed with solvent. The mobile phase comprises a solvent, which can be aqueous or organic, that flows through the interstitial space that exists between the spaces occupied by the stationary phase.

Columns with associated end caps, fittings and tubing are the most common configuration, with the media packed into the tube or column. The mobile phase, is pumped through the column. The sample is introduced at one end of the column, the feed end, and the various components interact with the stationary phase by any one of a multitude of adsorptive phenomena. The differential adsorptive interaction between the components and media leads them to traverse the column at different velocities, which results in a physical separation of the components in the mobile phase. The separated components are collected or detected at the other end of the column, the eluent end, in the order in which they travel in the mobile phase. In one type of adsorptive process, referred to as capture and release process, the process involves multiple steps, first to load the media, then to wash it, and then to elute it.

Chromatographic methods include among other methods, gel chromatography, ion exchange chromatography, hydrophobic interaction chromatography, reverse phase chromatography, affinity chromatography, immuno-adsorption chromatography, lectin affinity chromatography, ion affinity chromatography and other such well-known chromatographic methods.

Adsorptive media comes in many forms, most typically in the form of beads. The beads are conventionally packed into columns, with the column walls and ends imbolizing the beads into a fixed adsorptive bed, a bed being a porous 3 dimensional structure containing the stationary phase (in this case the beads) and the pore space through which the mobile phase flows/permeates (the space between the beads). Adsorptive media may also be formed into cohesive beds that retain their shape by virtue of the cohesion in the media; just like beds made with beads, these beds have two distinct regions, one occupied by the stationary phase and another occupied by the mobile phase; this type of media are referred to as monolithic media, or simply as monoliths. Media may also be formed in the shape of fabrics or webs, which can be stacked to form an adsorptive bed. Beds made of monoliths are cohesive in 3 dimensions, whereas beds made of webs are cohesive only in 2 dimensions; beds made of beads alone have no cohesion, requiring the column to maintain its shape. The processes and devices of this invention require that the beds be (at least) planarly cohesive—i.e. cohesive in 2 dimensions—enabling the formation of planarly cohesive adsorptive blocks.

Planar adsorptive processes and devices have been in use. Examples of planar adsorptive processes are paper chromatography and thin layer chromatography. In these processes, the adsorptive bed has a planar geometry in contrast to the cylindrical geometry of conventional chromatography beds. The mobile phase typically flows through the stationary phase by virtue of the capillarity of the porous medium, which draws the solvent into the porous space of the media. These processes do not require that the fluid pressure be contained since the fluid is not being pumped. More recently, a form of planar chromatography has been developed in which the fluid is pumped; this process is referred to as over-pressure planar chromatography (OPPC). OPPC requires that the media be contained in apparatus that maintains the shape of the bed in spite of the pressures used. In all cases, the planar adsorptive beds used in these processes are very thin, usually no thicker than a millimeter, making them suitable for analytical applications.

Membrane-based adsorptive devices have been developed. In these devices the adsorptive media is either supported by or embedded into a flat micro-porous membrane, which is then fabricated into filtration devices. Two or more of these membranes may be stacked to form an adsorptive bed with a longer flow path; however, the number of layers that can be stacked is limited by the low hydraulic permeability of microfiltration membranes. Such filtration devices are characterized by the fact that the fluid being treated flows through the adsoprtive media in a direction substantially perpendicular to the planar dimension of the media. The virtue of membrane adsorbers is their fast kinetics, enabling them to have short bed depths and high feed rates. However, the same attributes that confer them with fast kinetics severely and limit their capacity. Additionally, the intrinsic geometry of existing membrane adsorbers limit their scalability, the largest ones typically being no larger than 5 liters.

Furthermore, the bed depth, or absorptive path length, important in purification steps requiring resolution, is limited in membrane-based devices due to the low hydraulic permeability of microporous membranes. Membrane absorptive media is expensive, because the high cost of the membrane substrate and the challenges of functionalizing the membrane surface with absorptive chemistry. Finally, membrane-based adsorptive devices inherently have low capacity, as a result membrane adsorption devices have found applicability primarily in "polishing" steps—e.g. virus and DNA removal—where the adsorptive load is negligible, rather than in the core capture/purification steps.

Conventional chromatographic devices require that beads must be packed into a column. The quality of this packing determines the performance of the adsorbing bed. This adds another source of variability to the chromatographic process and must be validated before use. Furthermore, beds packed with beads are prone to voiding, a phenomenon whereby the beads settle into a denser structure resulting in the creation of voids and in nonhomogeneities in the packing density of the bed, all of which results in a deterioration of performance. This is especially true in columns packed with soft beads.

SUMMARY

The special demands imposed on pharmaceutical manufacturing processes make it highly desirable that such processes be easily scaled-up. In particular, there are many advantages to processes that can be scaled-up without having to reset or redevelop the processing conditions. Such processes are referred to in the industry as linearly-scalable processes; in essence, the parameters that define the separation process and operating conditions remain unchanged as the process moves from the laboratory bench (i.e., discovery), where the column can be as small as several milliliters, to the process development laboratory (e.g., columns of several liters), to clinical manufacturing, to large-scale manufacturing, where the chromatography column can be as large as several hundred liters. Existing chromatographic devices are not linearly scaleable, their design and geometry requiring significant alterations as the device size increases, thereby introducing uncertainties and unwanted risks as processes evolve from drug discovery, to clinical trials, to small-scale and then to large-scale manufacturing.

It is the object of this invention to design an adsorptive device suitable for chromatography that is linearly-scalable over a large dynamic range. It is a further object of this invention to make it easy for end-users to increase the capacity of a system without having to upgrade the whole system by simply stacking the same adsorptive devices. It is a further object of this invention to design adsorptive devices with adsorptive media that is rigid, will resist the compression of the hydraulic pressures and that will not void, enabling the use of soft stationary phases, e.g. agarose, at high pressures. It is a further object of this invention to design devices that are easy to load and unload on the equipment in which the devices are being used, and to make the attachment simple and reliable to prevent operational problems. These and other features of the invention will become apparent in the detailed description below.

An adsorptive device, according to one embodiment, includes at least one block comprising planarly cohesive, substantially isotropic adsorptive media, the block including a first end; a second end; a first substantially planar surface; a second substantially planar surface; at least one sidewall substantially perpendicular to the first and second planar surfaces; a first plurality of distribution passageways disposed within the at least one block, adjacent the first end and substantially perpendicular to the first and second planar surfaces; a second plurality of distribution passageways disposed within the at least one block adjacent the second end and substantially perpendicular to the first and second planar surfaces; and a peripheral seal encapsulating the at least one sidewall. Such a device can be linearly scaled to operate from the process development laboratory scale, to clinical manufacturing, to large-scale manufacturing.

Aspects of the present invention relate to absorptive devices that have the high capacity of beads but the operational advantages of webs, and in particular webs that have the properties of native agarose in rigid form. Other aspects of the present invention relate to linearly scalable devices and absorptive devices that provide the flexibility to develop new purification processes beyond the conventional batch chromatography processes.

Embodiments of the invention include media in web form (as compared to beads) producing significant fabrication and structural benefits. In one embodiment the webs are stacked in cassette devices to form beds of significant thickness, exceeding several millimeters, and as large as tens of centimeters to create adsorptive devices in the form of a "cassette". These adsorptive beds capable of being formed into beds of significant thicknesses are herein referred to as adsorptive blocks or blocks. Since the cassettes have significant thickness, the webs include distributor passageways in the height dimension (i.e. in the "stacking" dimension for the case of webs). In this embodiment, the webs have impermeable edges adhered to them. This feature allows the webs to support themselves against the tensile stresses generated by the pressure within the cassette on the sidewalls, requiring no additional structure to support the sidewalls of the cassettes.

In another embodiment, an adsorptive device for processing a fluid includes a pair of end plates, each plate including a feed end, a feed inlet disposed at the feed end, an eluent end, and an eluent outlet disposed at the eluent end, a plurality of cassettes in a stacked configuration, each cassette includes planarly cohesive, substantially isotropic adsorptive media; a first substantially planar surface, a second substantially planar surface substantially parallel to the first substantially planar surface, a first plurality of distribution passageways within each of the plurality of cassettes, the passageways fluidly coupled to the feed inlet, a second plurality of distribution passageways within each of the plurality of cassettes, the passageways fluidly coupled to the eluent outlet; the planar surfaces of each of the plurality of cassettes having the same shape; a peripheral seal encapsulating a sidewall of each of the plurality of cassettes to contain the fluid under operating pressures; wherein cassette geometry and location of the passageways induce substantially uniform lateral flow from the feed end to the eluent end within the block, the uniform lateral flow being parallel to the first and second substantially planar surface; and one of the pair of endplates is adjacent to a first surface of the block and a second one of the pair of endplates is adjacent to a second surface of the block. Such a device enables processing much larger volumes of fluids with a single device.

A method of forming a planarly cohesive, substantially isotropic adsorptive media block, according to one aspect of the invention, includes providing a plurality of planarly cohesive, substantially isotropic webs having an edge, a first end and a second end; cutting the webs to a predetermined dimension; stacking the webs to form a stack of webs; forming a peripheral edge seal adjacent to the web edges; and forming distributor passageways at a first end and at an opposite second end. Such a technique enables the manufacture of scalable chromatography devices. Another aspect of the invention is related to an integrated assembly of cassettes, hereby referred to as a "multiplexed cassette", particularly suitable for SMBC (Simulated Moving Bed Chromatography).

BRIEF DESCRIPTION OF DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings. The following drawings are illustrative of embodiments of the invention and are not meant to limit the scope of the invention as encompassed by the claims.

FIG. 1A is a schematic diagram of a perspective top view of an adsorptive device according to an aspect of the invention;

FIG. 1B is a schematic diagram of a bottom view of the adsorptive device of FIG. 1;

FIGS. 2A and 2B are schematic diagrams of cross sectional views (along section 2A-2A) of the device of FIG. 1A;

FIG. 3A is a schematic diagram of a side view of an adsorptive device for processing a fluid according to an aspect of the invention;

FIGS. 3B and 3C are schematic diagrams of cross sectional views (along section 3B-3B and along section 3C-3C) of the device of FIG. 2A showing details of the end plates and manifolds;

FIGS. 7-11 are schematic diagrams showing alternative geometries, media types and flow profiles of cassettes according to other aspects of the invention;

FIGS. 12-13 are schematic diagrams showing alternative fabrication methods of devices according to the invention;

FIG. 14 is a schematic diagram showing a cassette assembly according to an aspect of the invention;

FIGS. 15-16 are schematic diagrams showing the multiplexed cassettes according to aspects of the invention.

DETAILED DESCRIPTION OF THE INVENTION

Figure 4:
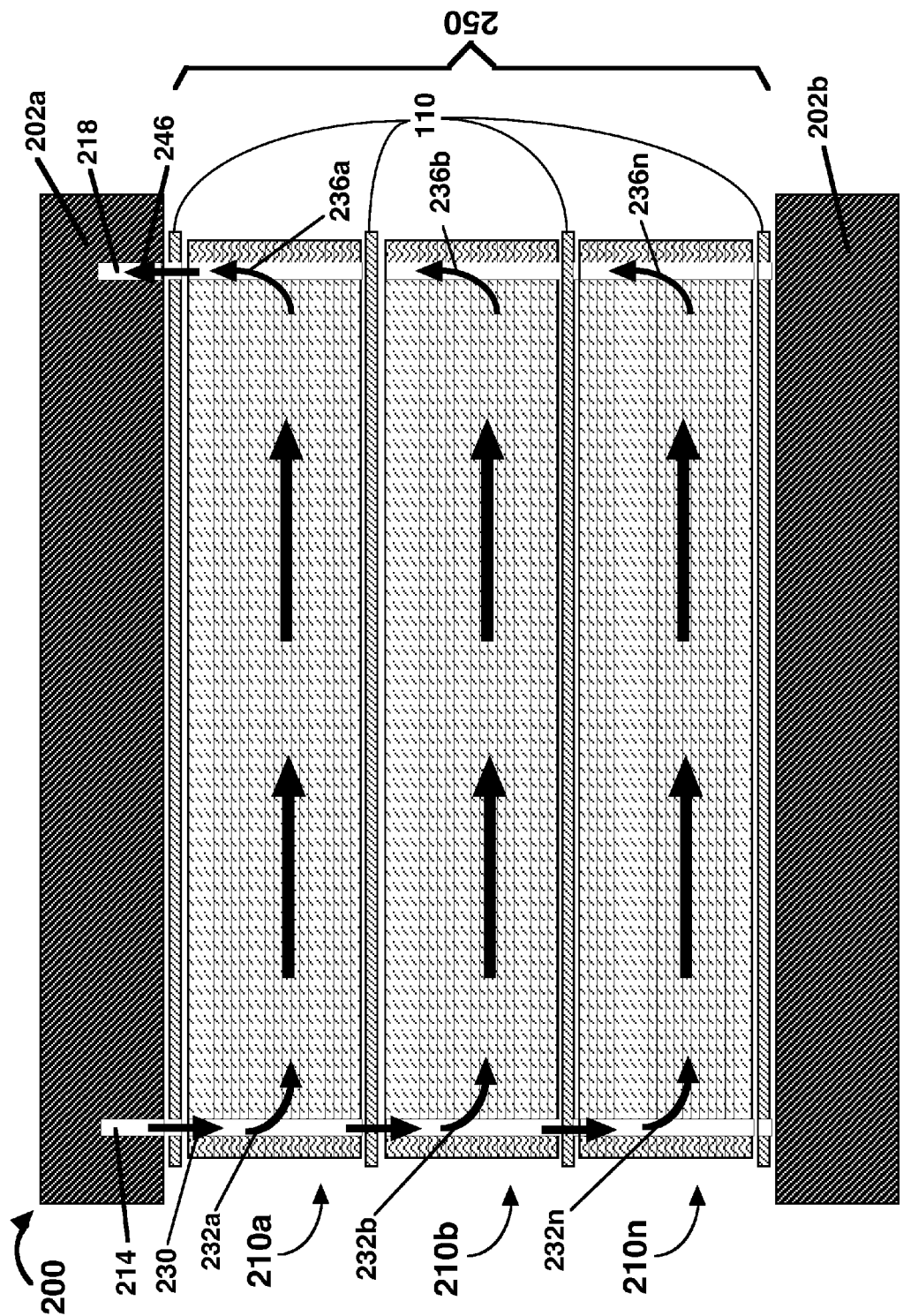
FIG. 4 is an elevation view of a stack of cassettes hydraulically in parallel forming a composite cassette.

This invention specifically relates to devices and processes suitable for preparative and manufacturing processes, and more specifically to processes used in the manufacture in the pharmaceutical industry for the production of medicinal or therapeutic products.

In contrast to conventional devices, applicants have discovered a way to support adsorptive media in a configuration that is linearly scalable and self supporting. Embodiments of the invention utilize planarly cohesive media. A web of adsorptive media, as for example, Macro-IPN media, is planarly cohesive. The media retains its shape even when pulled apart by a tensile force. A monolith is also planarly cohesive, except that it is much thicker than a bed. The cohesion plane of planarly cohesive media is oriented in parallel to the planar surfaces of the adsorptive device. The cohesiveness of the media along the cohesion plane enables the fabrication of adsorptive media blocks as described below.

The term adsorptive media, chromatography media, and media are herein used interchangeably to refer to the stationary phase of an adsorptive device; media can also refer a single type of medium. As used herein, intimate contact generally refers to the scale of the void space left between adjacent layers, and means that these void spaces are of the same order of magnitude as the scale of the interstitial space occupied by the mobile phase within the beds. The term solvent and mobile phase are used herein interchangeably to refer to the mobile phase. The term lateral flow means fluid flow within the media along the cohesion plane; for example, in web-based adsorptive media lateral flow means flow along the plane of the web, in contrast to flow that is perpendicular to the plane of the web. The term adsorptive block and adsorptive device and cassette are used interchangeably to refer to the planarly cohesive beds of adsorptive media used in devices of this invention. The term isotropic means that the porous media through which the fluid flows has a homogenous porous structure perpendicular to the direction of flow, such that the specific resistance to flow is independent of the location within the media in planes perpendicular to the direction of flow; the importance of isotropic media is elaborated upon further below. By substantially it is meant that the deviations of the values of the property being described are sufficiently small to enable the adsorptive device to perform as expected.

Referring to FIGS. 1A-1B, an adsorptive device 10 includes at least one block 20 comprising planarly cohesive, substantially isotropic adsorptive media 21, the block has a first end 12, a second end 16, a first substantially planar surface 22, a second substantially planar surface 23, at least one sidewall 26 substantially perpendicular to the first and second planar surfaces 22, 23. The block further comprises a first plurality of distribution passageways 14a-14n (collectively referred to as distribution passageway 14) disposed within the at least one block 20, adjacent the first end 12 and substantially perpendicular to the first and second planar surfaces 22 and 23, a second plurality of distribution passageways 18a-18n (collectively referred to as distribution passageway 18) disposed within the at least one block 20 adjacent the second end and substantially perpendicular to the first and second planar surfaces 22 and 23, and a peripheral edge seal 28 encapsulating the at least one sidewall 26 having a planar surface portion 24.

The alignment and location of the distribution passageways 14 and 18 with respect to each other and the geometrical shape of the first and second planar surfaces 22 and 23 (also referred to as the footprint) are designed to induce substantially uniform lateral flow of fluid within the block 20 from the first end 12 to the second end 16. The block 20 may have a variety of footprints, for example, rectangular, circular, trapezoidal, etc. The shape of the footprint in conjunction with the location of the distribution passageways 14 and 18 are the design factors responsible for inducing the desired uniform flow.

The block 20 is a three-dimensional device characterized by a length 32, a height 30 and a width 34. The direction of fluid flow is aligned with the length coordinate; the width of the planar surfaces 22 and 23 defines the width 34 and the height 30 of the block 20 is the dimension perpendicular to the planar surfaces 22 and 23.

In operation, fluid is introduced and distributed into distribution passageways 14 and collected and removed from distribution passageways 18. The adsorptive device 10 is rendered "self-supporting" by the encapsulation of the sidewall 26 defined by the cohesion planes, parallel to the planar surfaces 23 and 23, of the planarly cohesive, substantially isotropic adsorptive media 21. The blocks 20 of adsorptive device 10 do not require additional support structures to contain the hydraulic pressures generated in use, enabling the blocks 20 to be easily loaded and unloaded between end plates shown below in conjunction with FIG. 3A. This attribute additionally allows the stacking of blocks 20 without a change of the end plates enabling very easy scale-up.

It is understood that in an adsorptive device 10 there are numerous possible paths, or streamlines, between the distribution passageways 14 and 18. The fluid in each streamline takes a certain amount of time to complete the trajectory from the first end 12 to the second end 16, this time being typically referred to as the residence time. High performance adsorptive devices require that the variation in the residence time of all the streamlines be as small as possible. To achieve this performance attribute, adsorptive blocks should have adsorptive media that is substantially isotropic along planes perpendicular to the direction of flow, in addition to having streamlines that have substantially uniform length. Flow uniformity is the net result of this combination of properties.

In one embodiment the layers of adsorptive media are formed from web-based adsorption media, for example, macroporous IPN media produced in a web and cut to fit the block 20. Macroporous IPN media is described in PCT application PCT/US2010/024804 entitled POROUS INTERPENETRATING POLYMER NETWORKS WITH IMPROVED PROPERTIES, filed Feb. 19, 2010, which is incorporated by reference in its entirety. In other embodiments the layers of adsorptive media might comprise Empore discs (3M Corp., St. Paul, Minn.), or Whatman Chromatography Paper (GE Life Sciences, Westborough Mass.).

FIG. 2A shows a magnified section view (through Section 2A-Section 2A of FIG. 1A) of distribution passageways 14 on the first end of block 20. FIG. 2A shows a cross section of block 20 having four layers of web 29. FIG. 2B shows a block 20' having more layers of web 29 and therefore a higher height than the block 20 shown in FIG. 1A. Block 20 can include multiple web layers 29a-29n (collectively referred to as web layer 29) of the planarly cohesive, substantially isotropic adsorptive media 21.

The feed stream (not shown) is distributed along the width of the block 20 by manifold 120 (shown below in conjunction with FIG. 3B) entering each one of several passageways 14a-14n as a feed sub-stream, which is further distributed and turned forming lateral flow streams within each web layer 29. In contrast to filtration devices, lateral streams 8 flow along the plane that defines web layer 29 (i.e., these flow laterally rather than perpendicularly to the plane of web layer 29).

FIG. 2B shows adsorptive device 10' which includes additional web layers 29 as compared to adsorptive device 10 of FIG. 2A.

Now referring to FIGS. 3A-3C, an adsorptive device 100 for processing a fluid includes a pair of end plates 102a and 102b (also referred to as end plate 102). Each end plate 102 has a feed end 105 and an eluent end 107. At least one of the pair of end plates 102 has a feed inlet 106 disposed at the feed end 105, and at least one of the pair of end plates 102 has an eluent outlet 108 disposed at the eluent end 107. The adsorptive device 100 further includes a plurality of cassettes 200 in a stacked configuration (shown here as a single cassette 200, stacked configurations described below in conjunction with FIGS. 3, 4 and 5).

Each cassette 200 is similar to the block 20 of FIG. 1A. As described above, the cassette 200 geometry and location of the passageways induce substantially uniform lateral flow from the feed end 105 to the eluent end 107 within the block, the uniform lateral flow being parallel to the first and second substantially planar surface. Here, one of the pair of end plates 102a is adjacent to the first surface 22 of the cassette 200 and a second one of the pair of end plates 102b is adjacent to a second surface 23 of the cassette 200.

Still referring to FIGS. 3A-3C, cassette 200 further comprises peripheral edge seal 28 forming an impermeable seal of web 29 (also called "seal" and "peripheral edge seal") using a sealant. In one embodiment a thermoset resin is used and in another embodiment a thermoplastic resin is used to form the seal. Other sealants known in the art can also be used. Peripheral edge seal 28 is adhered to web 29 forming a structural boundary to include the elevated pressures present inside the cassette. Cassette 200 further comprises passageways 14 and 18 distributed along its width at both the feed and eluent ends, respectively, and are used for the introduction of the feed stream and collection of the eluent stream along the width of cassette 200. Passageways 14 (also referred to as distribution passageways) penetrate cassette 200 along its height from top to bottom, enabling the distribution of fluid along the height H.

FIG. 3B shows a sectional side view of a manifold 120a disposed in end plate 102a. Manifold 120a is used to introduce the feed stream 130a, whereas manifold 120b disposed on the opposite end of end plate 102a is used to recover the eluent stream 130b, as shown in FIG. 3C. Flow passages 124a inside manifold 120a are used to distribute the feed stream to distribution passageways 14 in cassette 200. Flow passages 124b inside manifold 120b are used to collect the eluent stream from distribution passageways 18 in cassette 200. It is understood that there are several different operational configurations of the manifold 120a and 120b in the end plates 102a and 102b.

In certain embodiments, cassettes 210a-210n are stacked such that they are hydraulically in parallel as shown in FIG. 4 (hereafter referred to as a "parallel configuration"). In this case cassettes 210 form a composite cassette 250 whose height is equal to the sum of the heights of each cassette 210. Manifolds 120a and 120b (FIG. 3A) are used to support stacked cassettes 210 by means of support structure (not shown), which can be made of tie rods or of some sort of external press), and include passageways (not shown) to distribute the feed stream into the distribution passageways on the feed end and to collect the eluent stream from the eluent end of cassettes 210. Manifolds 120 have a feed and an eluent end to match the feed and eluent ends of cassettes 210.

Feed and eluent distribution passageways 14 and 18 can be configured in several positions in the end plates. Both can be located only in the top manifold, or only in the bottom manifold. Alternatively, feed distribution passageways can be located only on the top end plate with eluent distribution passageways only on the bottom end plate or any combinations thereof, as long as there is at least one set of feed distribution passageways and one set eluent distribution passageways in either the top or bottom manifolds disposed within the end plates. Gaskets 110 may be used to obtain a reliable seal between adjacent cassettes 210 and between cassettes 210 and manifolds. Gaskets 110 may be integrated (and adhered) into each cassette 210, or may be a separate component that is added as part of a stack of cassettes 210 to form a block. To enable cassettes 210 to be stacked in the fashion shown in FIG. 4, these must be approximately of the same length and width, and the distribution passageways need to be similarly located so that they line up and are in fluid communication; however, it should be understood that while FIG. 4 shows cassettes 210 of the same height, cassettes can be of different heights.

Figure 5:
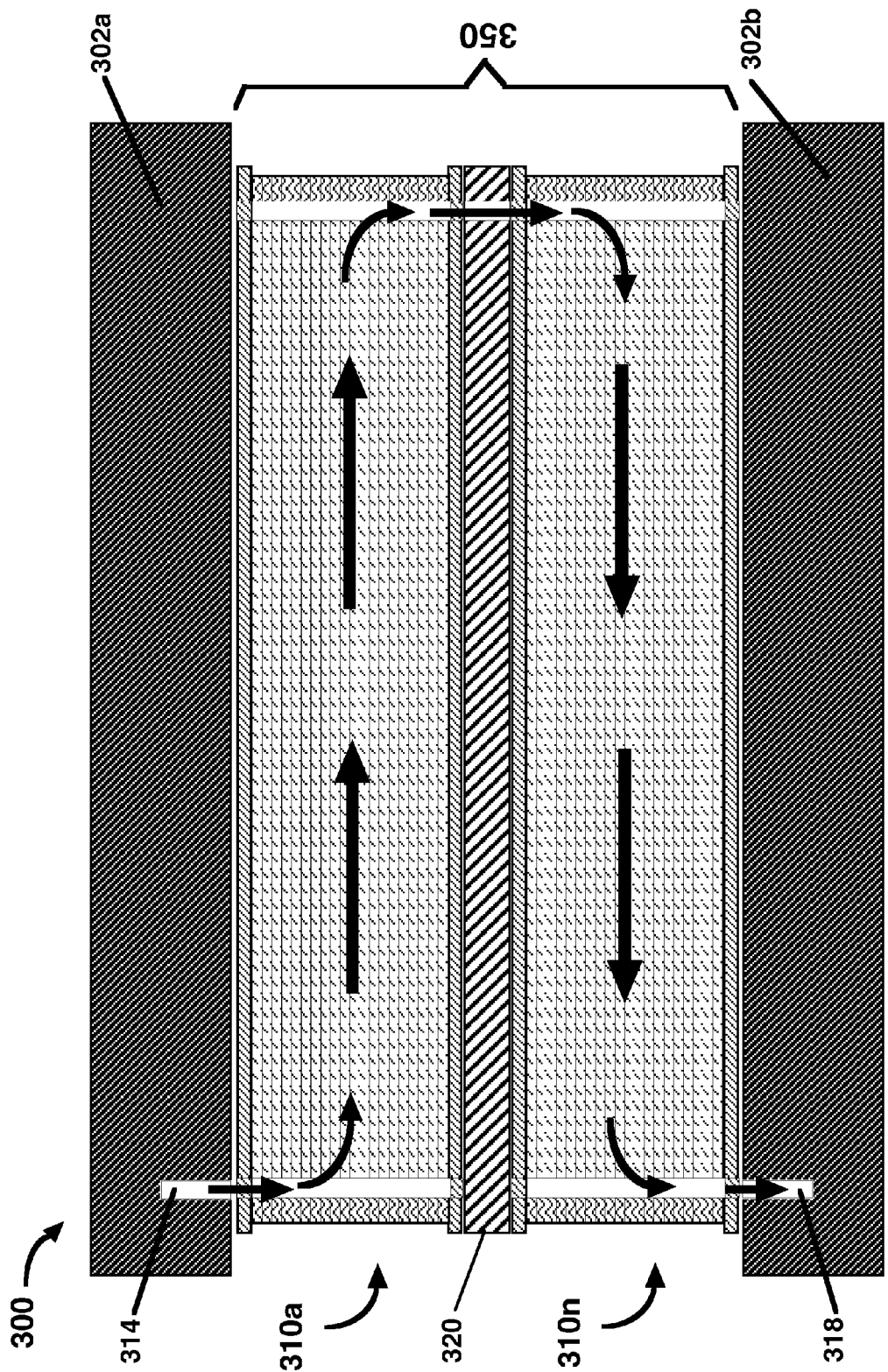
FIG. 5 is an elevation view of a stack of cassettes hydraulically in series forming a composite cassette.

Alternatively in other embodiments, cassettes are stacked such that they are hydraulically in series as shown in FIG. 5. In this case cassettes 310a-310n form a composite cassette 350 whose hydraulic length is equal to the sum of the lengths of each cassette 310 by virtue of flow diverter plate 320. Manifolds (not shown) are used to support stacked cassettes 310 by means of support structure (not shown), and include distribution to distribute the feed stream into the distribution passageways 314 on the feed end and to collect the eluent stream from the eluent end of cassettes 310. End plates have a feed and an eluent end to match the feed and eluent ends of cassettes 310. In contrast to the parallel configuration shown in FIG. 4, feed and eluent passageways must be located in separate manifolds. Gaskets 110 may be used to obtain a reliable seal between adjacent cassettes 310, between cassettes 310 and flow diverter plates 320, and between cassettes 310 and end plates. Gaskets 110 may be integrated (and adhered) into each cassette 310, or may be a separate component that is added as part of a stack of cassettes to form a block. To enable cassettes 310 to be stacked in the fashion shown in FIG. 5, these must be approximately of the same length and width, and the distribution passageways need to be similarly located so that they line up and are in fluid communication. However, it should be understood that while FIG. 5 shows cassettes 310 of the same height, cassettes can be of different heights; furthermore, two or more cassettes can be placed in series.

It is understood that it is possible to create composite cassettes utilizing combinations of parallel and series configurations as shown in FIGS. 4 and 5 by introducing flow diverter plates 320 at desired locations within a stack of cassettes 310.

Figure 6:
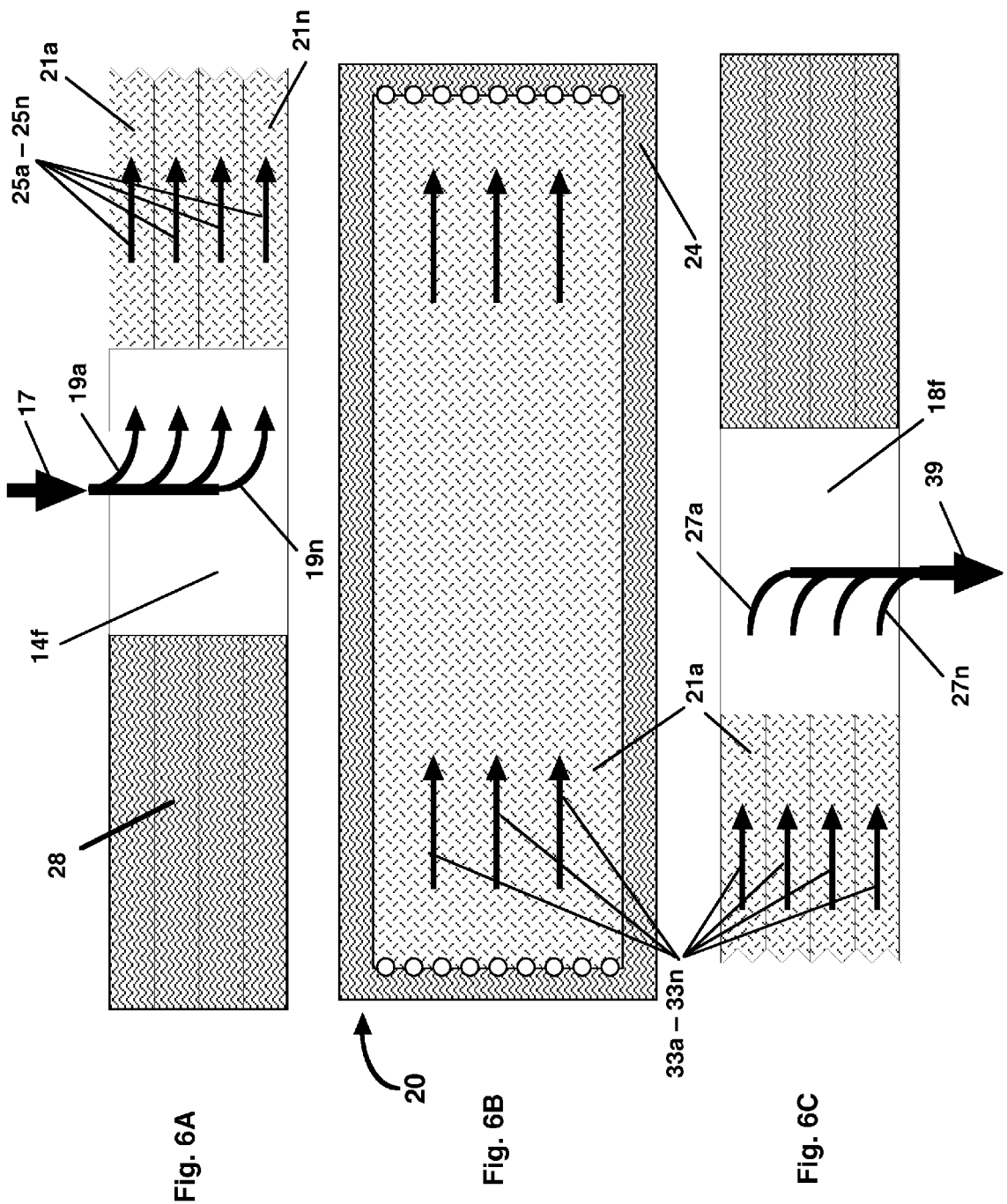
FIGS. 6A-6C are schematic diagrams showing flow profiles in cassettes according to an aspect of the invention.

FIG. 6A shows a magnified section view (through Section 2A on FIG. 1B) of distribution passageway 14f on the feed end of block 20, showing the flow profile of the feed stream within each web 21a-21n. The feed stream (not shown) is distributed along the width of the block by the manifold (not shown) entering each one of several distribution passageways 14 as feed sub-stream 17, which is further distributed and turned forming lateral streams 25a-25n within each web layer. In contrast to filtration devices, lateral streams 25a-25n flow along the plane that defines web 21 (i.e., these flow laterally rather than perpendicularly to the plane of web 21). FIG. 6B shows the flow streamlines 21a-21n in plan view on web 21, showing the fluid traveling from the feed end towards the eluent end. FIG. 6C shows a magnified section view (through Section 2A on FIG. 1B) of distribution passageway 18f on the eluent end of block 20, further showing how lateral streams 33a-33n within each web layer 21 are collected to form eluent sub-stream 39 within distribution passageway 18f. There are multiple eluent sub-streams 39 that are collected along the width of the cassette by the manifold (not shown) forming the complete eluent stream (not shown) from block 20.

Figure 7:
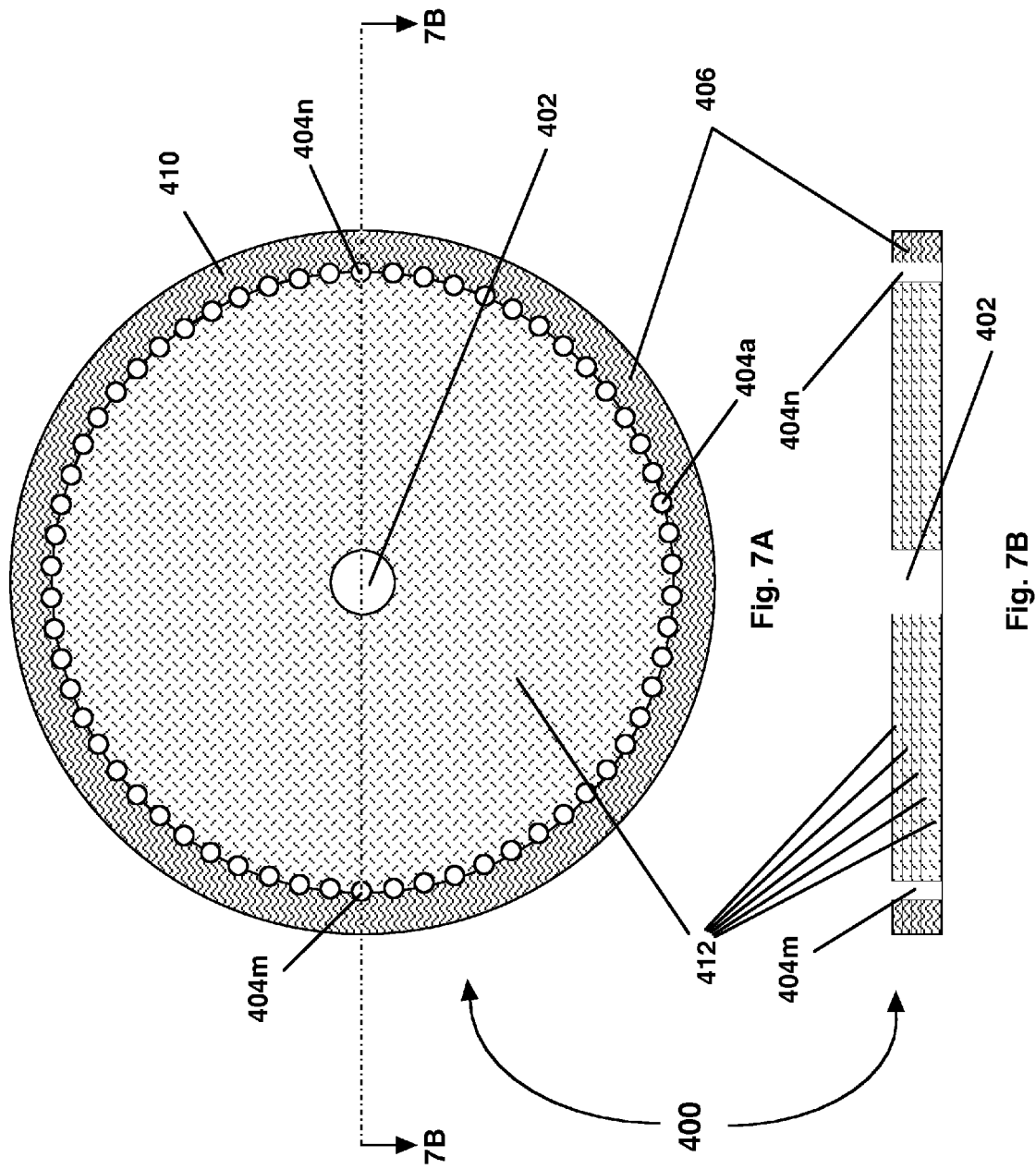

FIG. 7 shows another embodiment of this invention, where the cassette is configured in a circular geometry instead of a rectangular geometry as shown in FIG. 1A. Circularly shaped web 412 has a peripheral edge seal 410 with distribution passageways 404a-404n. In this case the feed distribution passageways 404 are located in the periphery of web 412, whereas the eluent distribution passageway 402 may be a single channel in the center of web 412 (it should be understood that the distribution passageway 402 in the center of the circular web may also comprise two or more distribution passageways 402). Alternatively, the passageway 402 in the center is the feed distributor whereas the passageways 404 near the periphery are the eluent distributors. In this case the fluid flow path is radial, making the length of the flow path approximately equal to the radius of the circularly shaped web 412.

Figure 8:
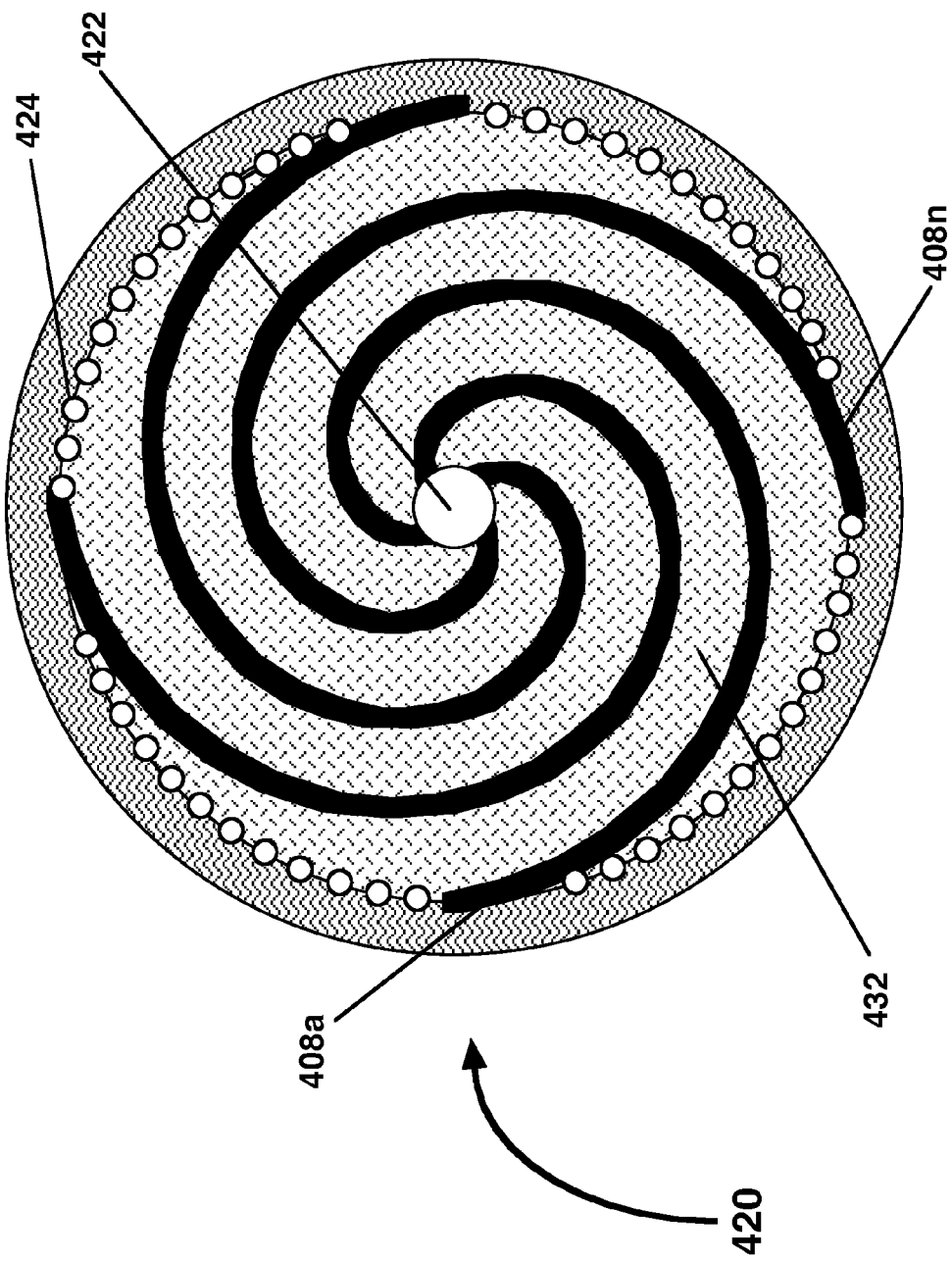

FIG. 8 shows another embodiment of a circularly shaped cassette including ribs 408a-408n that force the fluid to flow in a spiral trajectory forming a longer flow path than that on the embodiment shown in FIG. 7.

FIG. 9 shows another embodiment of a cassette 440 whose webs 452 are approximately in the shape of a "pie slice" or a trapezoid. Any shape is possible as long as webs 452 are flat, have peripheral edge seal 448 and distribution passageways 444 and 446, the application dictating which shape is most beneficial. Also, in general it should be understood that ribs (not shown) can be utilized in any geometry, circular, rectangular or otherwise, to channel the fluid in trajectories which may be different from the natural trajectory that a fluid would travel within the webs 452.

FIG. 10 shows a cassette 500 according to one embodiment of this invention made with an adsorptive media in the form of a monolith 522 instead of multiple web layers, the key difference being that monolith 522 is much thicker than a web, such that a single monolith creates a substantial height (only possible with multiple layers when using webs). According to this embodiment monolith 522 comprises peripheral edge seal 506 and distribution passageways 508, FIG. 8B showing a cassette made with a monolith thinner than that shown in FIG. 8C. Just as has been described in FIGS. 1 through 7, cassettes of the same geometries and possibilities can be made with monoliths 522 as long as these have flat top and bottom surfaces and have sufficient tensile and compressive strength to support the hydraulic forces generated in use. Monoliths create the option of adding a seal to the flat top and bottom surfaces capable of restraining the hydraulic forces generated in use. In this case the top and bottom plates become optional since the cassette is self-supporting; furthermore, the end plates only need to attach to the feed and eluent distributors in cassette 500.

FIG. 10 shows a cassette 500' according to one embodiment of this invention made with an adsorptive media in the form of a monolith 522 instead of multiple web layers, the key difference being that monolith 522 is much thicker than a web, such that a single monolith creates a substantial height (only possible with multiple layers when using webs). According to this embodiment monolith 522 comprises peripheral edge seal 506 and distribution passageways 508, FIG. 10B showing a cassette made with a monolith thinner than the cassette 500' shown in FIG. 10C. Just as has been described in FIGS. 1 through 7, cassettes of the same geometries and possibilities can be made with monoliths 522 as long as these have flat top and bottom surfaces and have sufficient tensile and compressive strength to support the hydraulic forces generated in use. Monoliths create the option of adding a seal to the flat top and bottom surfaces capable of restraining the hydraulic forces generated in use. In this case the top and bottom plates become optional since the cassette is self-supporting; furthermore, the end plates only need to attach to the feed and eluent distributors in cassettes 500 and 500'.

FIG. 11A shows a plan view of another embodiment of a rectangularly-shaped cassette in which the cassette is "double-sided." In this embodiment the cassette includes another set of center distribution passageways 516 at the center point of the length dimension of web 512 in addition to the set of distribution passageways 504 and 508 at the two ends of the cassette 500. Referring to FIG. 11A cassette 550 comprises webs 512 with peripheral edge seal 513 having a set of center distribution passageways 516 at the center point of the length dimension of web 512, and two sets of distribution passageways 504 and 508 at the two ends of web 512. In this particular embodiment center distribution passageways 516 distribute the feed stream, while end passageways 504 and 508 collect the eluent stream. Flow profiles for this embodiment are shown in FIG. 11B. In an alternative embodiment of a double-sided cassette (not shown), distribution passageways 504 and 508 distribute the feed streams while center passageways 506 collect the eluent streams.

FIGS. 12A-12E represents in schematic manner an exemplary process to fabricate the cassette shown in FIG. 1A. A plurality of webs 600 are cut to a desired dimension as shown FIG. 12A and stacked as shown in FIG. 12B. A peripheral edge seal 606 is created by one of many methods known to those skilled in the art (e.g., thermoset resins or thermoplastic resin or other sealants known to those skilled in the art can also be used) as shown in FIG. 12C. Once cured, the stack of webs 600 is perforated (by drilling, die cutting, laser cutting or other methods known to those skilled in the art) to form substantially straight distribution passageways 604 and 608 in the height dimension as shown in FIG. 12D, resulting in finished cassette 620 of FIG. 12E.

Figure 13A:
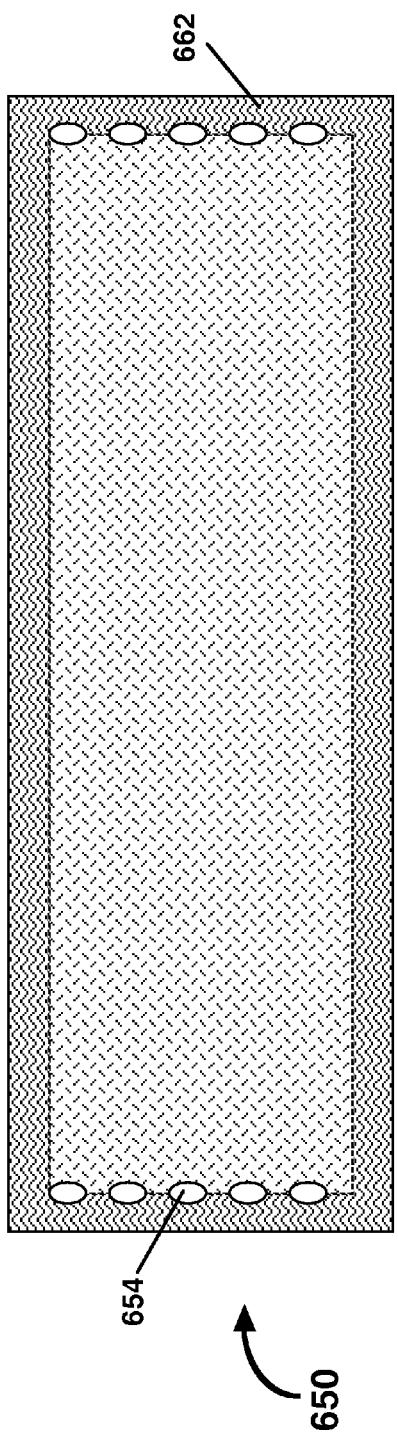
Figure 13B:
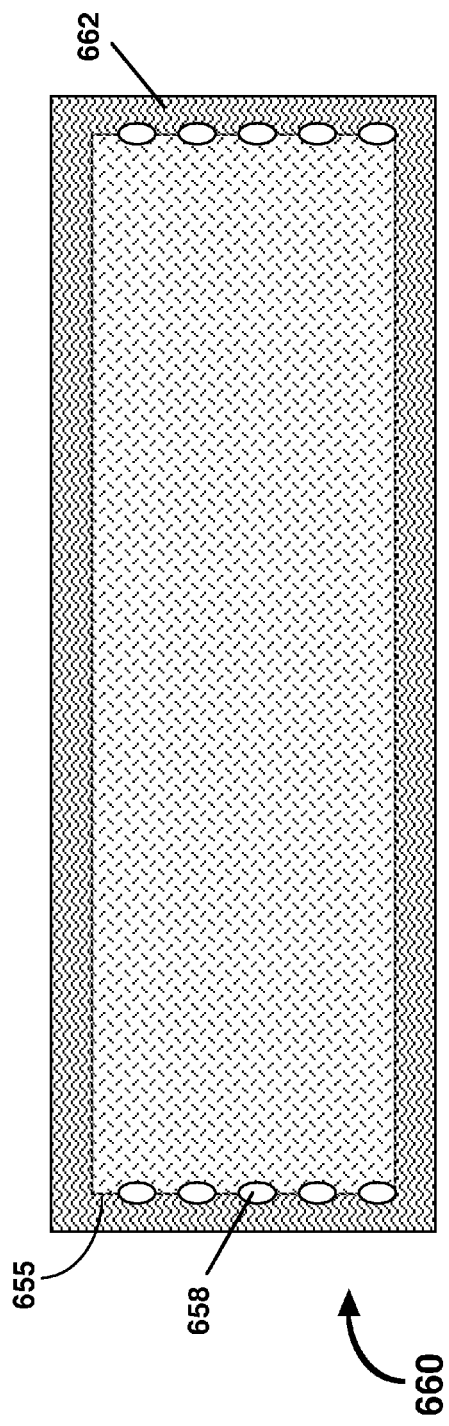

There are many variations to this fabrication method. For example, the distribution passageways may be perforated on each individual web 650 before these are stacked; this method allows the formation of distribution passageways that are not identically located in each web 650, which is acceptable as long as the distribution passageways 654 and 658 have some overlap enabling fluid communication when adjacent webs 650 and 660 are stacked, as shown in FIGS. 13A and 13B. Referring to FIG. 13A, web 650 is perforated with oblong distribution passageways 654, which are not centered in the width dimension but are closer to one edge of web 650 than the other edge, whereas web 660 shown in FIG. 13B is perforated with the same oblong distribution passageways 658 which are also not centered (according to offset 655), but displaced towards the opposite edge of web 660. When adjacent webs 650 and web 660 are stacked, the distribution passageways 654 and 658 do not line up perfectly on top of each other, but do overlap to still create a distributor that is in fluid communication. It should be appreciated that perforating the web 650 with distribution passageways 654 and 658 before stacking the webs provides a large flexibility in the formation of the distributors which may be of advantage in some applications. Likewise it may be advantageous to add peripheral edge seal 662 to each web individually before these are stacked.

Distributors may add to band spreading, a phenomenon that deteriorates the effectiveness of chromatographic separation, a deterioration that increases as the hold-up volume of distributors becomes larger relatively to the volume in the separation medium. Therefore, distributors should be designed to have the lowest volume. However, this needs to be balanced with the pressure drop generated by a distributor, which becomes larger the smaller the diameter of the distribution passageways. In many cases, it is possible to maintain the distributor volume to be small relative to the rest of the adsorptive medium, and in such cases, the exact distribution pattern of the feed and eluent streams within the distributor has little impact on the separation performance of the devices. In such cases, it is of little consequence where the fluid enters and exits the cassette.

Another approach to reduce the deterioration produced by distributors is to design them such that the bands are not distorted, even when the distributor volume is not small. This requires that every streamline within the separation device (the separation media and the distributor, including the flow passages/distributors contained within the end plates) have the same residence time. For devices of this invention, wherein the feed stream comes from a point source and the eluent stream goes back to a point source, the location of entry and exit of the feed and eluent streams, respectively, may be important, leading to preferred embodiments for the distributor design. In the case of rectangular devices of this invention (e.g. as shown in FIGS. 1 through 4), to maintain the residence time at every streamline as uniform as possible in the presence of significant hold-up volume in the distributors the design principle that should be followed is this: there should be mirror image symmetry in the flow pattern of the feed and eluent streams as they enter and exit the cassette along any plane bisecting the cassette in any of its dimensions. Specifically, this means two things: first, the feed and eluent streams should be located in opposing end plates, and secondly, the feed stream should enter the top (or bottom) end plate on the side opposite to that in which the eluent stream exits the opposite end plate.

FIGS. 14A, 14B and 14C show a device 700 comprising a cassette assembly according to one aspect of this invention with end plates designed according to the design principle described in the previous paragraph. FIG. 14A shows a sectional side view of cassette assembly 700, with top end plate 706a, a first gasket 705a, cassette 702, a second gasket 705b, and bottom end plate 706b. In this schematic diagram, top end plate 706a is used to introduce the feed stream, whereas bottom end plate 706b is used to recover the eluent stream. Flow passages 716a inside top end plate 706a is used to distribute the feed stream to distributor passageways 704a in cassette 702. Flow passages 716b inside bottom end plate 706b are used to collect the eluent stream from distributor passageways 704b in cassette 702. FIG. 14B is a front view of a cassette assembly 700 taken along section 14B in FIG. 14A. Referring to FIG. 14B, feed stream 707 enters end plate 706a at feed port 717, and then is further distributed along the width of the device utilizing flow passages 716a. Referring now to FIG. 14C, eluent stream 709 exits end plate 706b at eluent port 719, after having been collected along the width of the device utilizing flow passages 716b. FIGS. 14A, 14B and 14C clearly show that feed and eluent flow passages in end plates 706a and 706b are in mirror image symmetry one to the other as described in the previous paragraph, representing a preferred embodiment whenever the volume of the distributor passageways 704a and 704b in the devices of this invention lead to decreased separation performance. It should be further noticed that in this embodiment the flow direction of the feed and eluent streams is the same at every point within cassette assembly 702.

FIGS. 15A and 15B show another embodiment of this invention, according to which multiple cassettes 810a-810n are integrated into a single multiplexed cassette 800. Block 822 has peripheral edge seal 823 and further partitioned into multiple cassettes 810a-810n by means of inter-cassette seals 825. Distribution passageways 824 are perforated along the height of block 822 on both ends of block 822 in the manner shown in FIG. 15A. In this embodiment block 822 of multiplexed cassette 800 is built from a stack of multiple layers of web (not shown). Peripheral edge seals 823 and inter-cassette seals 825 are adhered to webs such that these can sustain the internal pressures present in cassettes 810a-810n during use. In another embodiment the media used to form the adsorptive block 822 may be in the form of a monolith (not shown) instead of webs.

Figure 16A:
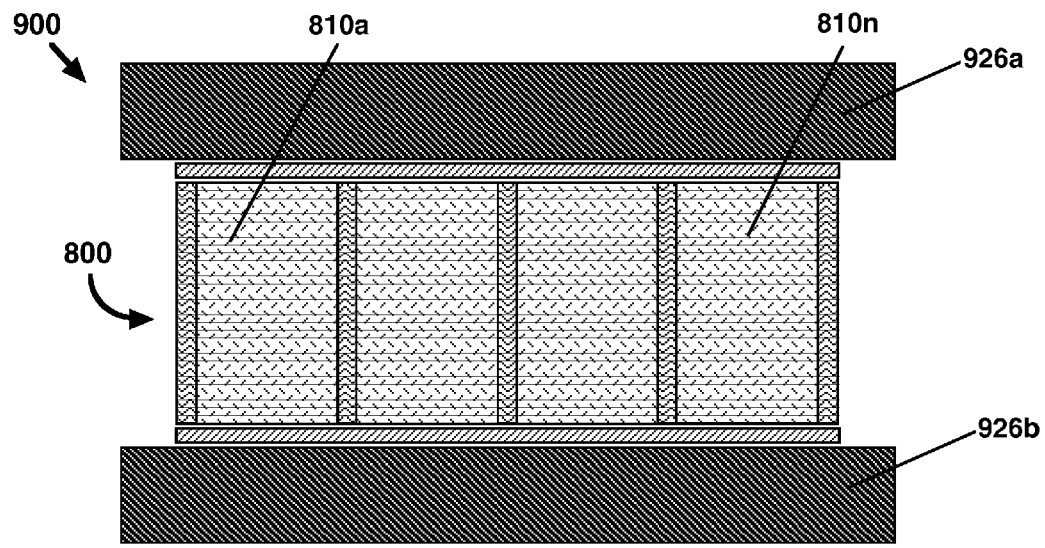
Figure 16B:
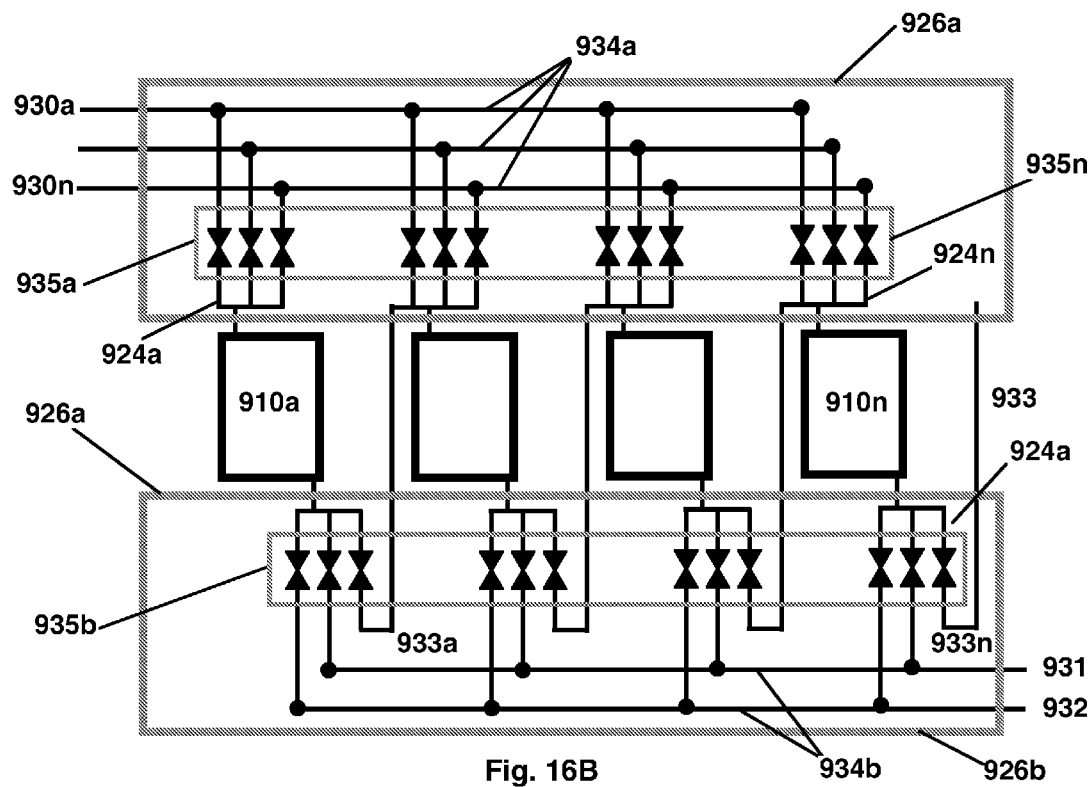

FIG. 16A is an elevation view of a multiplexed cassette 800 in combination with end plates 926a and 926b forming multicassette assembly 900. FIG. 16B is a schematic flow diagram of multiplexed cassette assembly 900. End plate 926a includes multiple passageways 934a for introducing multiple feed streams 930a-930n and an array of valves 935a-935n for diverting each feed stream into the manifold 924a of each one of cassettes 910a-910n (corresponding to cassettes 810a-810n of FIG. 16A. End plate 926b includes multiple passageways for collecting multiple eluent streams 934b from each one of cassettes 810a-810n and an array of valves 935b for diverting each eluent stream from the eluent distributors 924b into either a product stream 931, a waste stream 932, or possibly, a feed stream 933a-933n into another one of cassettes 910a-910n. The passageways and valves are included within the end plate, thereby liberating the user from having to make individual connections to each individual cassette 910a-910n. The process design dictates which valves are opened and closed, with a control system (not shown) that opens and close the valves accordingly. In some embodiments the end plates 926a and 926b are reusable. In other embodiments end plates 926a and 926b may be integrated with the cassette to form a completely disposable assembly 900, in which case valves 935a and 935b may be pneumatically actuated, with the pneumatic streams actuated by an array of reusable valves (not shown) connected to the disposable cassette assembly 900 by simple, quick-connect means known to those skilled in the art. This embodiment would be suitable for applications where cross-contamination between batches can't be tolerated, or where the cost of cleaning and validating the cleaning cycle is cost or time prohibitive, or when the safety of operating personnel demands that there be no exposure to the fluid streams.

In other embodiments a planarly cohesive adsorptive block is formed with a planarly cohesive scaffold packed with bead-based media. In one example, the planarly cohesive scaffold comprises bi-planar plastic netting, e.g. Vexar plastic netting (Conweb Plastics, Minneapolis Minn.). Plastic netting of this type is made of a biplanar array of polymer monofilaments forming a planarly cohesive net with open cells, typically square or rectangular cells. These nets can be stacked into a block with sidewalls perpendicular to the planar surfaces, which are then encapsulated with a suitable thermoset resin to form a planarly cohesive scaffold. The block comprising the empty scaffold is then packed with bead-based media. In this embodiment the scaffold renders the adsorptive media block planarly cohesive even though the beads are not. In still another embodiment, molded plates with open cells of similar size and orientation as those of plastic netting and edge seals are stacked and fusion bonded by methods known to those skilled in the art, forming a scaffold.

It is understood that although the embodiments described herein relate specifically to bio-molecular applications, the principles, practice and designs described herein are also useful in other applications, including the manufacture of vaccines and biopharmaceuticals. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. An adsorptive device comprising:
   at least one block comprising planarly cohesive, substantially isotropic adsorptive media, the block having:
   a first end;
   a second end;
   a first substantially planar surface;
   a second substantially planar surface;
   at least one sidewall substantially perpendicular to the first and second planar surfaces;
   a first plurality of distribution passageways disposed within the at least one block, adjacent the first end and substantially perpendicular to the first and second planar surfaces;
   a second plurality of distribution passageways disposed within the at least one block, adjacent the second end and substantially perpendicular to the first and second planar surfaces; and
   a peripheral seal encapsulating the at least one sidewall.

2. The device of claim 1 further comprising:
   a pair of end plates substantially parallel with the first and second planar surfaces, a first one of the pair of end plates adjacent to the first surface of the block and a second one of the pair of endplates adjacent to the second surface of the block, the pair of end plates supporting the block and comprising:
   a first manifold disposed in one of the pair of endplates, and fluidly coupling a feed inlet to the first plurality of distribution passageways; and
   a second manifold disposed in one of the pair of endplates and fluidly coupling an eluent outlet to the second plurality of distribution passageways.

3. The device of claim 1, wherein the first and second substantially planar surfaces are substantially parallel.

4. The device of claim 1, wherein the first and second plurality of distribution passageways are aligned and located with respect to each other to induce a substantially uniform lateral flow of fluid within the block from the first end to the second end.

5. The device of claim 1, wherein the peripheral seal contains a fluid under operating pressures.

6. The device of claim 1, wherein the planarly cohesive, substantially isotropic adsorptive media comprises planar, cohesive web media.

7. The device of claim 6, wherein the first plurality of distribution passageways and the second plurality of distribution passageways in adjacent webs overlap but do not line up exactly with the corresponding distribution passageways forming a passageway that is interconnected from the upper surface to the lower surface.

8. The device of claim 6, wherein the planarly cohesive web media is macroporous IPN media.

9. The device of claim 1, wherein the planarly cohesive, substantially isotropic adsorptive media comprises a monolithic media.

10. The device of claim 1, wherein the planarly cohesive, substantially isotropic adsorptive media comprises a planarly cohesive scaffold having voids packed with bead-based media, wherein the scaffold supports and restricts movement of the bead-based media.

11. The device of claim 1, wherein the at least one block has a thickness greater than about 5 millimeters.

12. The device of claim 11, wherein the at least one block has a rectangular shape.

13. The device of claim 1, wherein the at least one block has a thickness greater than about 10 millimeters.

* * * * *